(12) United States Patent
Corbitt et al.

(10) Patent No.: US 8,288,745 B2
(45) Date of Patent: Oct. 16, 2012

(54) METHOD OF UTILIZING AN IMPLANT FOR TARGETING EXTERNAL BEAM RADIATION

(75) Inventors: John Corbitt, Atlantis, FL (US); Lorl Anthony, Atlantis, FL (US)

(73) Assignee: Senorx, Inc., Irvine, CA (US)

( * ) Notice: Subject to any disclaimer, the term of this patent is extended or adjusted under 35 U.S.C. 154(b) by 1106 days.

(21) Appl. No.: 12/110,748

(22) Filed: Apr. 28, 2008

(65) Prior Publication Data

US 2008/0281388 A1  Nov. 13, 2008

Related U.S. Application Data

(60) Continuation-in-part of application No. 11/108,785, filed on Apr. 19, 2005, now Pat. No. 7,637,948, which is a continuation-in-part of application No. 10/627,718, filed on Jul. 28, 2003, now Pat. No. 6,881,226, which is a continuation of application No. 09/828,806, filed on Apr. 10, 2001, now Pat. No. 6,638,308, which is a division of application No. 09/169,351, filed on Oct. 9, 1998, now Pat. No. 6,214,045.

(60) Provisional application No. 60/061,588, filed on Oct. 10, 1997, provisional application No. 60/077,639, filed on Mar. 11, 1998, provisional application No. 60/091,306, filed on Jun. 30, 1998.

(51) Int. Cl.
*A61F 7/00* (2006.01)

(52) U.S. Cl. .......... 250/515.1; 250/492.1; 600/1; 600/2; 607/108; 623/7; 623/8; 623/23.75; 606/77; 424/400

(58) Field of Classification Search ............... 250/515.1, 250/492.1; 600/1, 2; 607/108; 623/7, 8, 623/23.75; 606/77; 424/400
See application file for complete search history.

(56) References Cited

U.S. PATENT DOCUMENTS

| | | | |
|---|---|---|---|
| 4,298,998 A | 11/1981 | Naficy | |
| 4,428,082 A | 1/1984 | Naficy | |
| 4,470,160 A | 9/1984 | Cavon | |
| 4,574,780 A * | 3/1986 | Manders | 128/898 |
| 4,740,208 A | 4/1988 | Cavon | |
| 4,795,463 A * | 1/1989 | Gerow | 623/8 |
| 4,863,470 A * | 9/1989 | Carter | 623/8 |
| 4,937,323 A * | 6/1990 | Silver et al. | 530/356 |
| 4,950,665 A | 8/1990 | Floyd | |
| 5,120,802 A | 6/1992 | Mares et al. | |
| 5,147,398 A * | 9/1992 | Lynn et al. | 623/8 |
| 5,192,744 A * | 3/1993 | Bouck et al. | 514/13.3 |
| 5,342,283 A * | 8/1994 | Good | 600/8 |
| 5,522,896 A | 6/1996 | Prescott | |
| 5,534,023 A * | 7/1996 | Henley | 623/8 |

(Continued)

FOREIGN PATENT DOCUMENTS

EP   0 475 077   3/1992

(Continued)

OTHER PUBLICATIONS

International Search Report of PCT/US2009/002551 mailed Jul. 10, 2009.

(Continued)

*Primary Examiner* — Michael Logie

(57) ABSTRACT

A novel method of partial breast radiation utilizing a breast implant which can provide a stable and improved target for stereotactic radiation treatment.

30 Claims, 8 Drawing Sheets

U.S. PATENT DOCUMENTS

| | | | |
|---|---|---|---|
| RE35,391 E | 12/1996 | Brauman | |
| 5,626,611 A | 5/1997 | Liu et al. | |
| 5,628,781 A | 5/1997 | Williams et al. | |
| 5,766,222 A * | 6/1998 | Petit | 606/234 |
| 5,824,081 A | 10/1998 | Knapp et al. | |
| 5,869,080 A * | 2/1999 | McGregor et al. | 424/426 |
| 5,922,024 A * | 7/1999 | Janzen et al. | 623/8 |
| 6,066,325 A | 5/2000 | Wallace et al. | |
| 6,099,457 A * | 8/2000 | Good | 600/8 |
| 6,161,034 A | 12/2000 | Burbank et al. | |
| 6,214,045 B1 * | 4/2001 | Corbitt, Jr. et al. | 623/8 |
| 6,220,248 B1 * | 4/2001 | Voegele et al. | 128/898 |
| 6,228,055 B1 * | 5/2001 | Foerster et al. | 604/116 |
| 6,316,522 B1 | 11/2001 | Loomis et al. | |
| 6,356,782 B1 * | 3/2002 | Sirimanne et al. | 600/431 |
| 6,403,758 B1 | 6/2002 | Loomis | |
| 6,638,308 B2 * | 10/2003 | Corbitt et al. | 623/8 |
| 6,881,226 B2 * | 4/2005 | Corbitt et al. | 623/8 |
| 7,044,957 B2 | 5/2006 | Foerster et al. | |
| 7,229,417 B2 | 6/2007 | Foerster et al. | |
| 7,297,725 B2 | 11/2007 | Winterton et al. | |
| 7,534,452 B2 | 5/2009 | Chernomorsky et al. | |
| 7,637,948 B2 * | 12/2009 | Corbitt, Jr. | 623/8 |
| 7,871,438 B2 * | 1/2011 | Corbitt, Jr. | 623/8 |
| 2001/0041936 A1 * | 11/2001 | Corbitt et al. | 623/8 |
| 2002/0022883 A1 | 2/2002 | Burg | |
| 2003/0036803 A1 | 2/2003 | McGhan | |
| 2004/0236211 A1 * | 11/2004 | Burbank et al. | 600/431 |
| 2005/0059887 A1 * | 3/2005 | Mostafavi et al. | 600/427 |
| 2005/0059888 A1 * | 3/2005 | Sirimanne et al. | 600/431 |
| 2005/0080338 A1 * | 4/2005 | Sirimanne et al. | 600/431 |
| 2005/0101860 A1 * | 5/2005 | Patrick et al. | 600/433 |
| 2005/0175657 A1 | 8/2005 | Hunter et al. | |
| 2005/0181007 A1 | 8/2005 | Hunter et al. | |
| 2006/0079829 A1 | 4/2006 | Fulton et al. | |
| 2006/0155190 A1 * | 7/2006 | Burbank et al. | 600/431 |
| 2009/0024225 A1 | 1/2009 | Stubbs | |

FOREIGN PATENT DOCUMENTS

| | | |
|---|---|---|
| JP | 08-500274 | 1/1996 |
| JP | 09-502371 | 3/1997 |
| WO | WO 94/16647 | 8/1994 |
| WO | WO 95/07057 | 3/1995 |
| WO | WO 99/35966 | 7/1999 |
| WO | WO 00/54689 | 9/2000 |
| WO | WO 2008/077081 | 6/2008 |

OTHER PUBLICATIONS

Written Opinion of the International Searching authority of PCT/US2009/002551 mailed Jul. 10, 2009.

Eiselt, P. et al, "Development of Technologies Aiding Large—Tissue Engineering", Biotechnol. Prog., vol. 14, No. 1, pp. 134-140, 1998.

* cited by examiner

METHOD OF UTILIZING AN IMPLANT FOR TARGETING EXTERNAL BEAM RADIATION

STATEMENT OF PRIORITY

This application is a continuation in part of U.S. patent application Ser. No. 11/108,785 filed on Apr. 19, 2005 now U.S. Pat. No. 7,637,948 which is a continuation in part of U.S. patent application Ser. No. 10/627,718 filed Jul. 28, 2003, now U.S. Pat. No. 6,881,226, which is a continuation of U.S. patent application Ser. No. 09/828,806 filed Apr. 10, 2001, now U.S. Pat. No. 6,638,308, which is a division of U.S. patent application Ser. No. 09/169,351, filed Oct. 9, 1998, now U.S. Pat. No. 6,214,045, which claims the benefit of U.S. Provisional Application Ser. No. 60/061,588, filed Oct. 10, 1997, U.S. Provisional Application Ser. No. 60/077,639 filed Mar. 11, 1998, and U.S. Provisional Application Ser. No. 60/091,306, filed Jun. 30, 1998, the disclosures of which are incorporated herein by reference.

BACKGROUND OF THE INVENTION

Radiation for breast cancer currently mainly consists of full breast radiation, which imparts radiotherapy to the full area of the breast. It necessarily involves surrounding structures such as, but not limited to the heart, lungs, esophagus, chest wall, ribs and other structures that are in close proximity to the breast. A new concept of partial breast radiation targeting the area of the breast involved by cancer is currently gaining popularity. Studies thus far indicate that it is as effective as full breast radiation and eliminates damage to the surrounding organs. Partial breast radiation is currently being delivered through temporarily implanted balloon catheters such as but not limited to the MAMMOSITE or the CONTURA. This process involves placing a radioactive seed or target down the catheter for a brief period of time, over three to five days. Unfortunately, this method of utilizing a catheter and radioactive seed has a number of drawbacks. Utilizing a concentrated dose of radiation over a short period of time in the form of a radioactive seed planted through means of the catheter or other surgical means creates a multitude of side effects such as fat necrosis, seromas, hematomas, infection and undesirable cosmetic outcomes. When a lumpectomy is performed, a temporary balloon catheter is put into place with the catheter extruding from the breast. This allows an opening into the cavity which increase the chance of infection. Furthermore, this method requires the physician to wait for the pathology report to indicate margins of the specimen to be free of cancer (as well as the absence of cancer from the lymph nodes) before the temporary balloon can be removed and a Mammosite, Contura or other external catheters can be implanted in preparation for partial breast radiation therapy. This sequence of procedures is preferred as soon as possible following lumpectomy. An additional drawback to the catheter methodology is the need to aspirate air from the lumpectomy cavity. Air in a lumpectomy cavity creates "hot spots" or high heat conditions within the cavity when subjected to radiation therapy, thereby causing burns and other undesirable side effects. Accordingly, it is desirable to aspirate or remove the air, most commonly with a syringe and needle. Unfortunately, the current method catheter may be punctured by the needle during aspiration, creating problems for its subsequent use and effectiveness in treatment. These problems are resolved by use of the proposed method. We propose the use of external beam radiation delivered through a multi-directional stereotactic radiation source such as but not limited to the CYBERKNIFE, the BRAIN LAB, and other external beam sources. However, external beam radiation requires a sufficiently identifiable target. Currently, external beam radiation is used on solid organs such as the liver that contains a tumor or the head of the pancreas that contains a tumor whereby a gold seed is implanted in these structures and acts as a guide for focusing the external stereotactic beam. The solid tissue of these organs provides a stable, non-shifting environment for placement of the seed which acts as a target for the external beam source. The use of the catheter in breast tissue has been previously necessary due to the presence of primarily fatty tissue in the breast, precluding a stable environment for placement of a small seed or target. In fatty tissue, a small seed or target would move from the intended target site, rendering the therapy ineffective. The breast is an external structure, constructed primarily of fatty tissue, unlike the other mentioned organs. Consequently, what is necessary then, is a means of stabilizing a seed or other target source within the fatty tissue of the breast, which seed or other target source may then be utilized as a target in a new method of partial breast radiation. The proposed invention addresses this problem. Being an external structure also, the breast is also capable of being more rigidly fixed for targeting in stereotactic radiation machines than the internal organs and is therefore a good candidate for utilizing partial irradiation through careful targeting of the internal implant and/or marker.

U.S. Pat. No. 6,214,045, issued to the applicant, discloses a breast implant of resorbable material sized to replace excised tissue and allowing for in-growth of fibrous tissue to replace the implant. The implant may be elastic, compressible, and expandable and may further contain diagnostic substances. The specification of U.S. Pat. No. 6,214,045 is incorporated by reference herein. Certain diagnostic substances are identified in the '045 patent as "x-ray opaque or metallic material for identification of the area." Many embodiments of the implants described in the '045 patent may act as appropriate targets for stereotactic radiation sources as radiopaque targets. Biodegradable materials such as, but not limited to, collagen and other suitably dense biocompatible materials, may be configured suitably radiopaque. The implants may alternatively be constructed of two or more different materials or contain large amounts of air, which will also aid in acquisition and targeting by a suitable stereotactic radiation source. The implant may be shaped spherical to keep the lumpectomy cavity open in a more uniform manner however this is not always necessary as the lumpectomy cavity created by a biopsy procedure can be allowed to partially collapse and conform to the size or shape of the implant. Consequently, the implant shape may guide the external beam source in order to allow a more specific area of the cavity to be radiated on one side or the other, or uniformly circumferentially in the event of utilizing a spherical implant. Particularly when compared with the previously disclosed catheter methodology, the ability to utilize variously shaped implants is superior to the catheter, which is spherically shaped, in the event it is necessary to construct a non-spherical lumpectomy cavity to obtain the desired margins upon removal of the cancer. The implant itself may act as the radio-opaque target or may have added to, more or less, the central portion of the implant, a tiny metallic marker such as but not limited to a gold seed or a titanium seed to further aid as a guide for the external beam. To conform with desired diagnostic needs and procedures, more than one marker may be utilized in a single implant or more than one implant, placed within the lumpectomy cavity. Different marker materials may be contained within a single implant or within more than one implant placed within the lumpectomy cavity. Any metallic material, suitably sterilized, or other relatively dense biocompatible material, may be utilized as a marker within the implant. Where the external beam radiation is utilized, it accomplishes local brachytherapy with its benefits and the beam can be configured over varying time periods so as to eliminate many of the complications associated with the current method of partial breast radiation, the balloon MammoSite or Contura. Use of the implants described in the '045 patent, addresses a multitude of the current problems known to the medical industry such as but not limited to cosmetic deformities, seromas, hematomas, infection and the like while simultaneously providing the stable target necessary for successful targeted radiation therapy. The 045 implants are configured to keep the cavity open and support the surrounding tissue. This is particularly important in radiation therapy as new tissue growth will be inhibited by the presence of radiation therapy. Accordingly, this method and use of the implant will enable the lumpectomy site to retain its configuration throughout radiation therapy and thereafter provide time for regeneration and in-growth of new tissue upon termination of radiation therapy. Once the external beam radiation is accomplished, the implant may biodegrade over a period of time allowing ingrowth of the patient's own natural tissues and, therefore reduce the risk of undesirable cosmetic changes to the overlying skin or the breast. It may also have added to the implant hemostatic agents to minimize bleeding, other metallic markers, oncologic agents, antibiotics and the like.

Another advantage in the use of the implant for targeted partial breast radiation therapy is that the biodegradable implant can be inserted into the breast at the time of the lumpectomy but radiation therapy my be delayed without presenting complications in the maintenance of the targeting means, treatment or to the patient. With the use of the catheter methodology, the externally extruding catheter and its prior discussed issues necessitates immediate radiation therapy treatment to minimize, to the extent possible, potential complications such as infection and discomfort to the patient. Immediate radiation therapy is not always preferred because the surgical wound is fresh and has not healed. The use of radiation further retards healing and promotes seroma formation, infection, and cosmetic defects because of poor healing. The proposed methodology, utilizing the implant, allows the implant to be placed in the lumpectomy cavity and the wound surgically sealed. The patient may maintain a normal lifestyle and radiation therapy may be scheduled as appropriate in the particular case. The patient may undergo chemotherapy and can delay radiation therapy up to about 120 days without decreasing the therapeutic effects of the radiation. The implant may degrade somewhat over a period of time while the breast is healing to allow the lumpectomy cavity to compress down upon the implant or scar down around the implant shrinking the cavity and stabilizing the target for future radiation. Future radiation therapy may be initiated many days or weeks after the lumpectomy. Radiation therapy may be discontinued, if necessary, and re-instituted as necessary, within the life of the biodegradable implant or, in the case of a marker, at any time thereafter. This accomplishes the prevention of hematomas or seromas, resulting in a better cosmetic outcome while maintaining a stable target for future therapy or diagnosis.

DETAILED DESCRIPTION OF THE DRAWINGS

Figure 1:
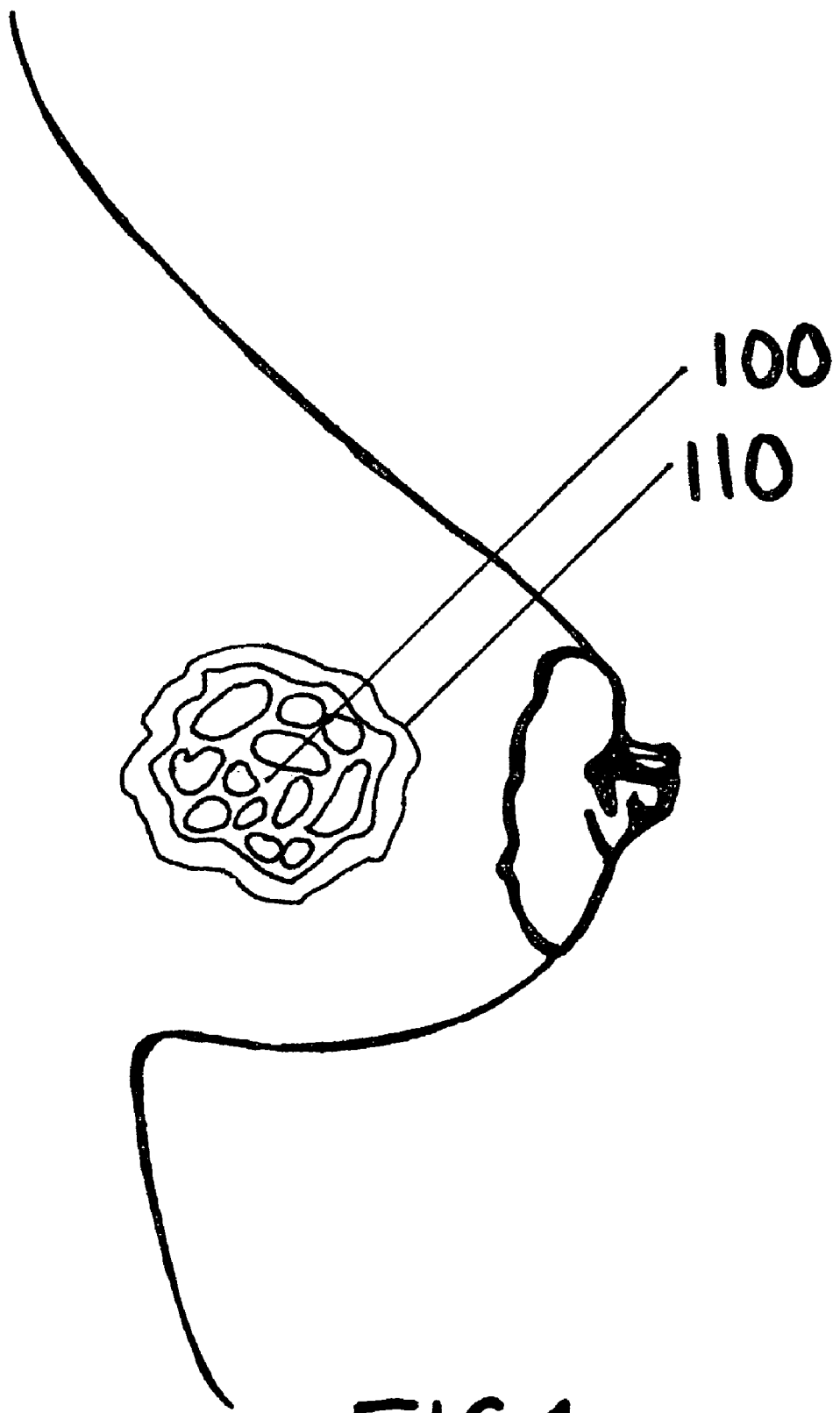
FIG. 1 depicts one embodiment of an implant placed within a breast lumpectomy cavity to act as a target for radiation therapy emissions.

In FIG. 1, a substantially spherical implant (100) is composed of biodegradable material and is placed within a breast lumpectomy cavity (110) following a biopsy or other surgical procedure. The implant may be constructed of materials such as biodegradable foams, sponges, gels, liquids, or other biocompatible substances. The material is formed in such a way that it can support surrounding breast tissue, assisting in breast cosmesis by keeping the breast lumpectomy cavity from collapsing. The implant further functions as a radio-opaque target for external beam stereotactic partial breast radiotherapy. The implant can be constructed with varying pore sizes thus allowing for example, more air to be incorporated into the implant, rendering the implant more radio-opaque while preventing the collection of air pockets within the breast cavity which create unsuitable conditions for radiation therapy. The implant does not need to be the exact size of the lumpectomy cavity, however. Breast tissue will collapse around the implant, keeping the cavity open and relatively equal distance from the center of the implant. The implant is of a sufficient size and solid consistency to allow a stereotactic radiation source to be directed to the implant as a target for delivery of radiation therapy to the surrounding margins of the lumpectomy cavity in a precise configuration as determined by the radiotherapist.

Figure 2:
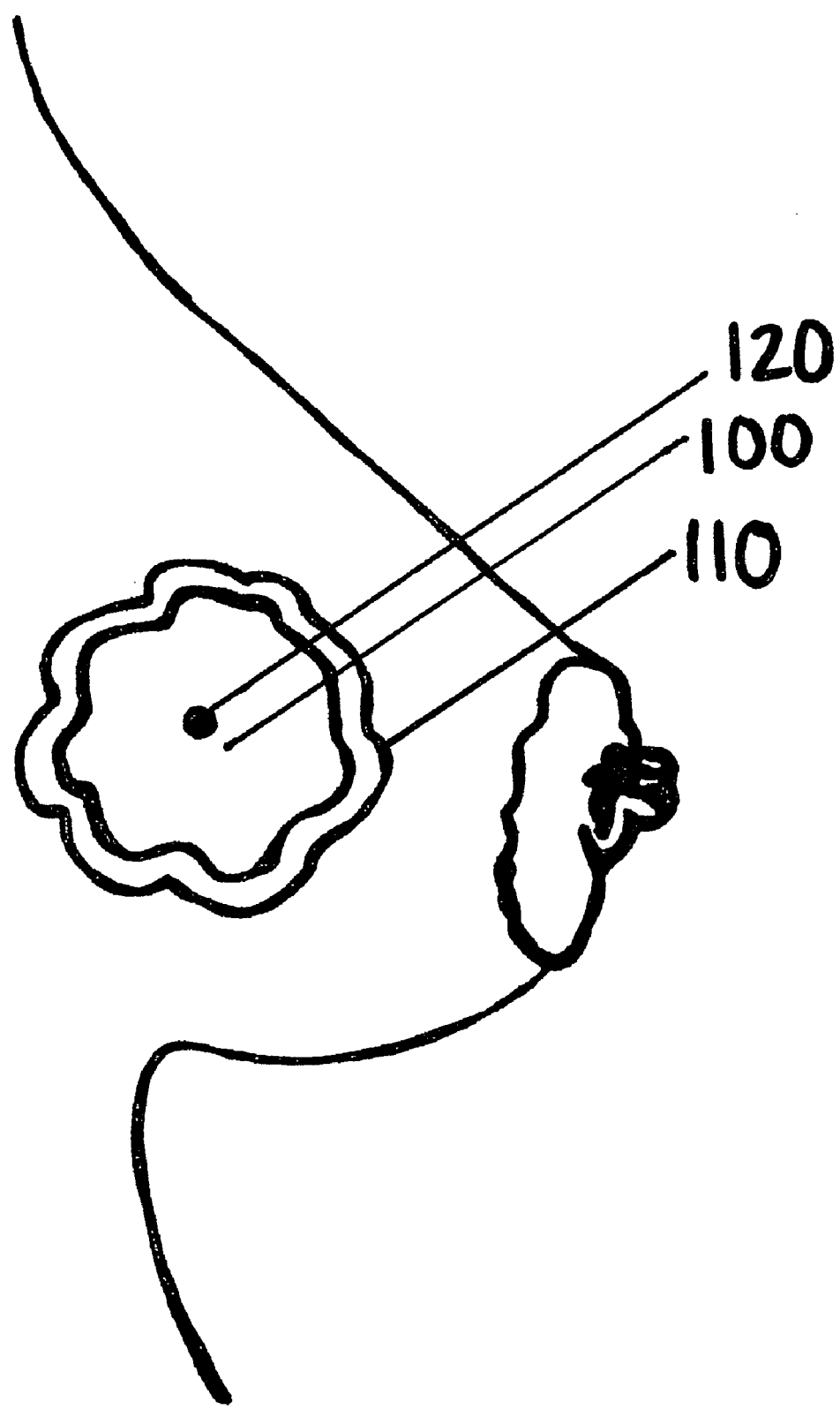
FIG. 2 depicts an alternative embodiment of an implant placed within a breast lumpectomy cavity and containing an internal marker to act as a target for radiation therapy emissions.

In FIG. 2, the implant (100) of FIG. 1 further contains a gold seed, metallic seed, titanium clip or other suitably dense implant material (120) to aid in successful targeting of the implant area for a stereotactic radiation source. Since margins can vary from patient to patient, the use of an implant material can serve as a guide for programming the stereotactic radiation unit. The target material may be centrally located within the implant or located about the periphery of the implant. One or more implant materials may be concurrently used as necessary to conform the intended radiation therapy to the patient's breast cancer treatment. As the target material may or may not be biodegradable, the implant material may remain available for extended radiation therapy as necessary. Biodegradable material may have variable absorption rates.

Figure 3:
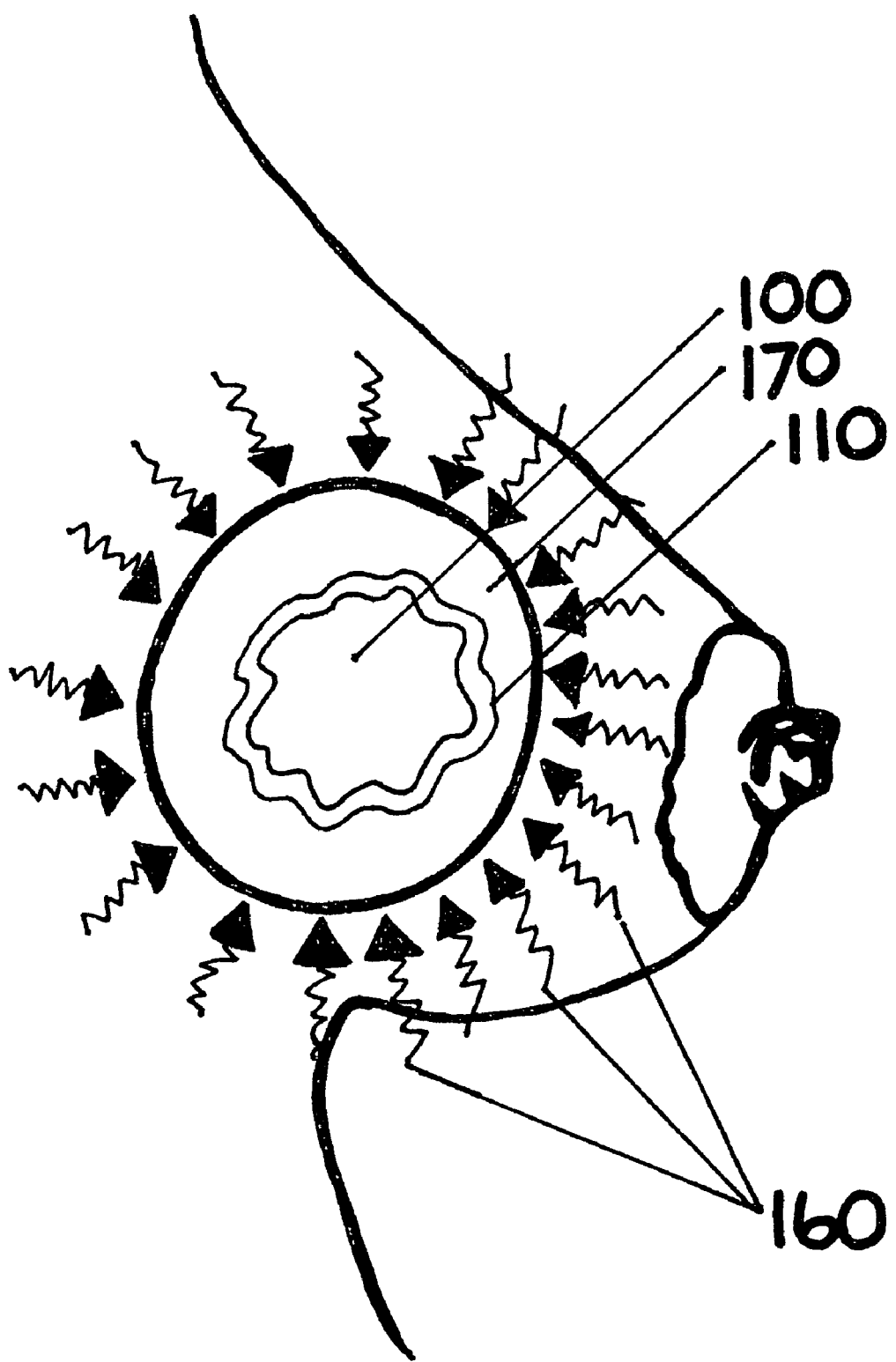
FIG. 3 depicts one example of an implant placed within a breast lumpectomy cavity and subjected to radiation therapy emissions.

In FIG. 3, an example of multi-directional (stereotactic) radiation therapy (160) targets a breast implant (100) in the breast lumpectomy cavity (110), partially irradiating the breast within targeted margins (170) around the lumpectomy cavity (110).

Figure 4:
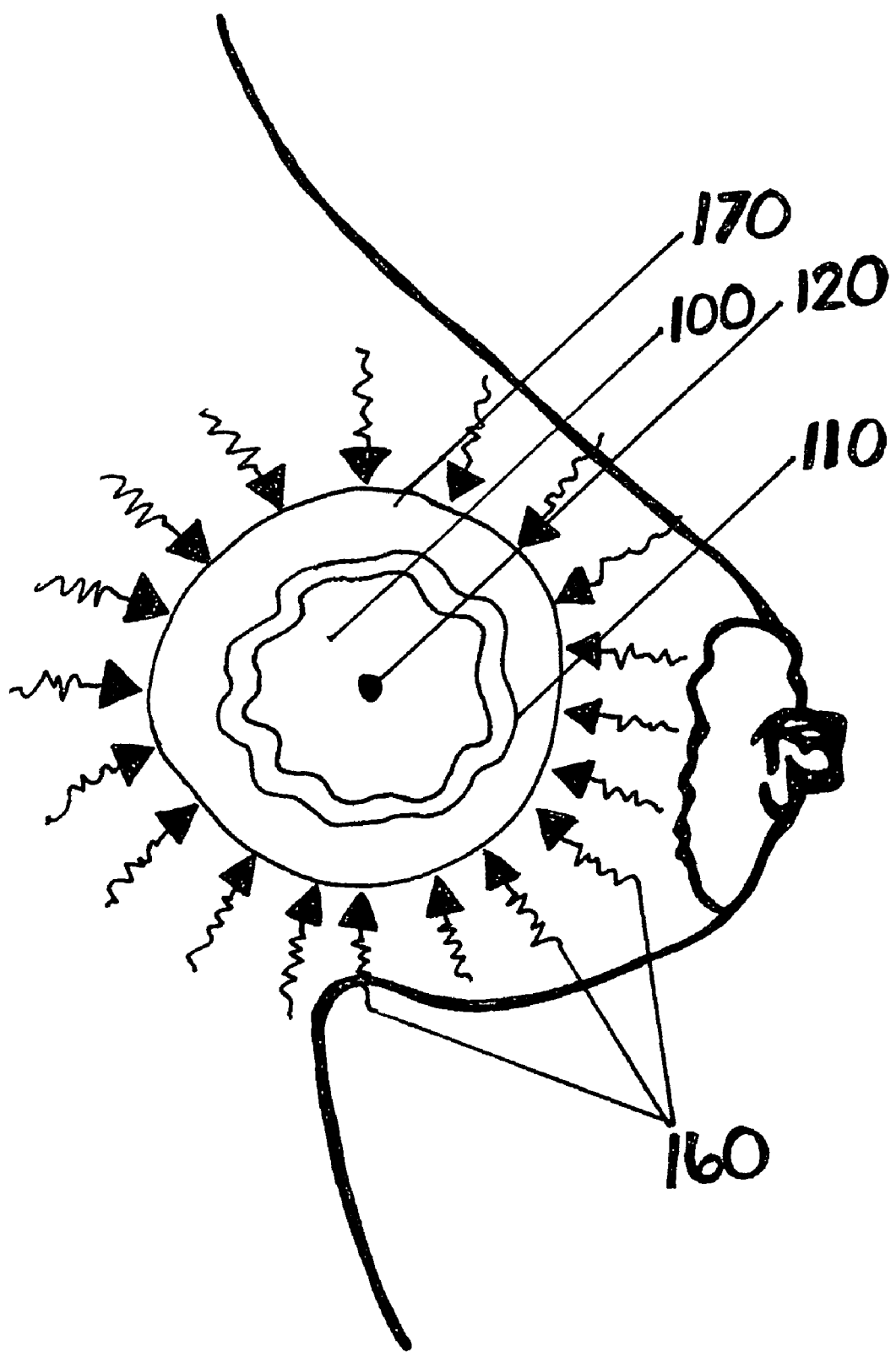
FIG. 4 depicts an alternative embodiment of an implant containing an internal marker to act as a target for radiation therapy emissions.

In FIG. 4, an example of multi-directional (stereotactic) radiation therapy (160) targets a breast implant (100) containing an internal marker (120), in the breast lumpectomy cavity (110), partially irradiating the breast within targeted margins (170) around the lumpectomy cavity (110).

Figure 5A:
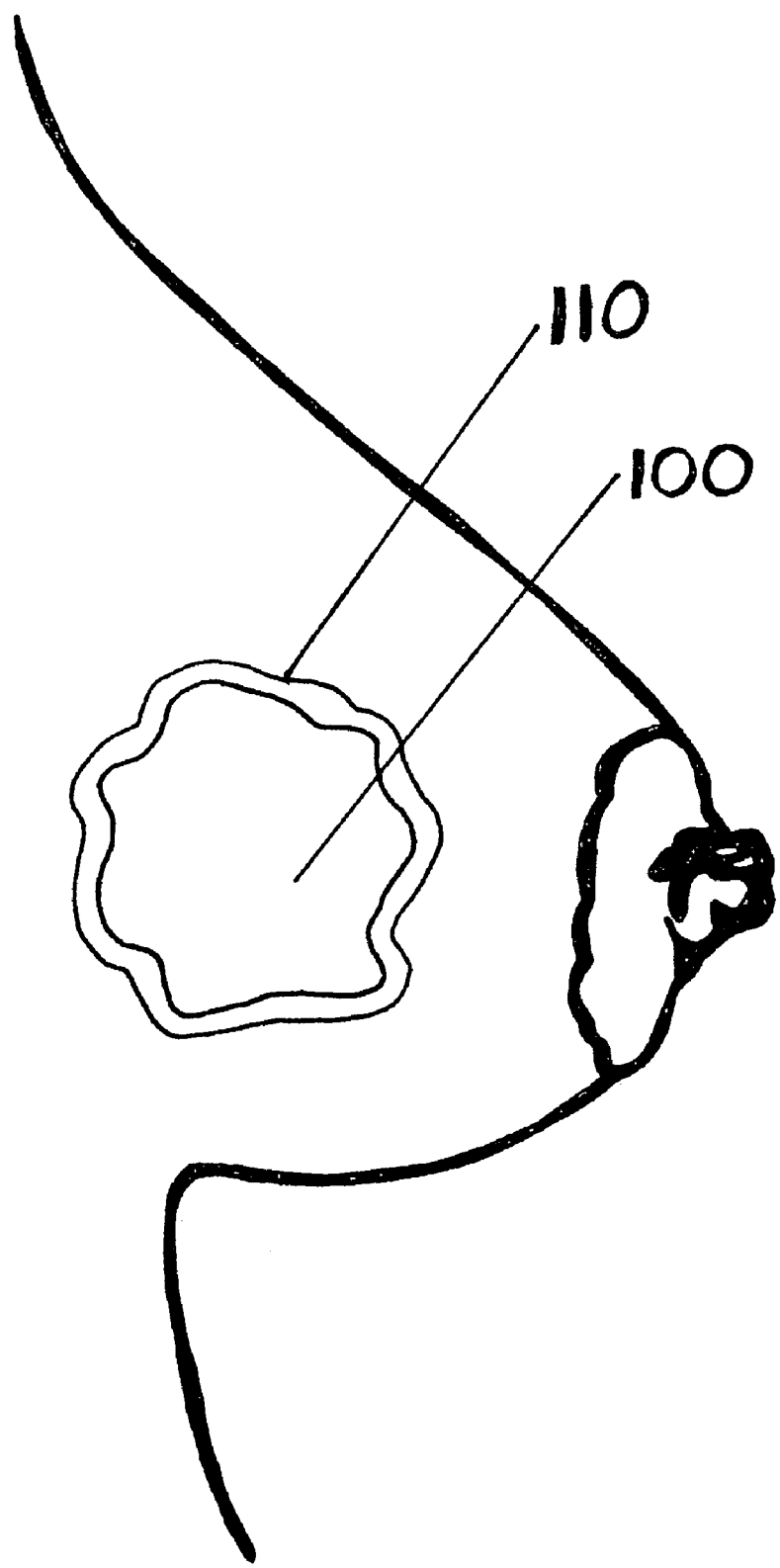
FIGS. 5A and 5B depict implants of various shapes and configurations placed within breast lumpectomy cavities.
Figure 5B:
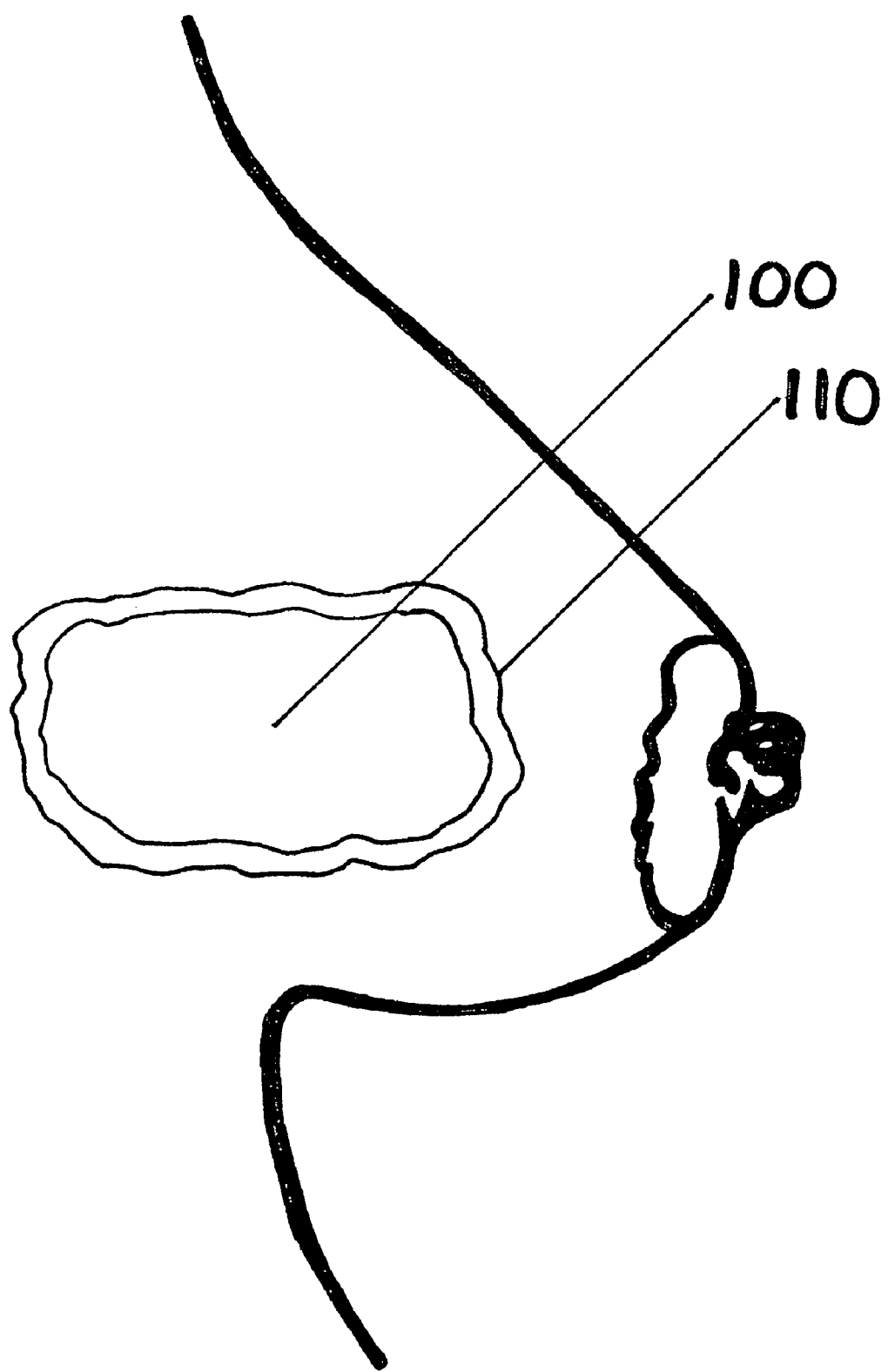

In FIG. 5A and FIG. 5B, an implant (100) in the breast lumpectomy cavity (110) may be configured to conform to the lumpectomy cavity excised to create sufficient margins for excision of cancer or in accordance with good medical practice for the surgical procedure. The ability to conform the implant to the cavity allows appropriate margins to be maintained for following radiation treatment and supports the surrounding breast tissue without deformation.

Figure 6:
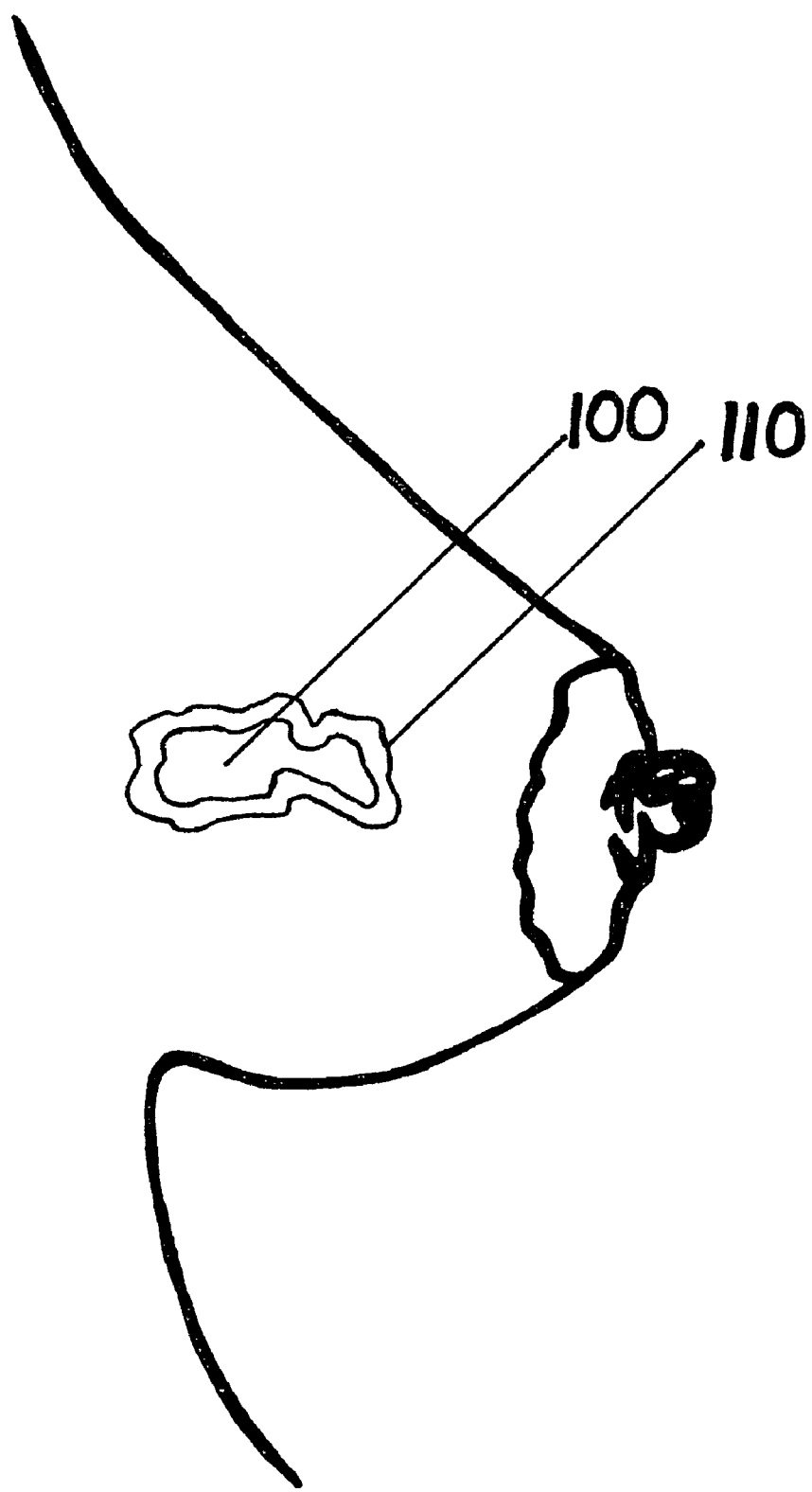
FIG. 6 depicts a partially re-absorbed implant within a shrinking breast lumpectomy cavity.

In FIG. 6, the implant (100) has partially reabsorbed as a consequence of the passage of time. Unlike the prior art catheter, the implant can act as a target to the biopsy site for weeks or months after implantation, to allow for healing, chemotherapy or other issues necessitating a delay in radiation treatment. The surrounding breast tissue comprising the lumpectomy cavity collapses or generates growth as the implant resorbs, holding the implant in place and the geometry of the breast tissue in static relation.

Figure 7:
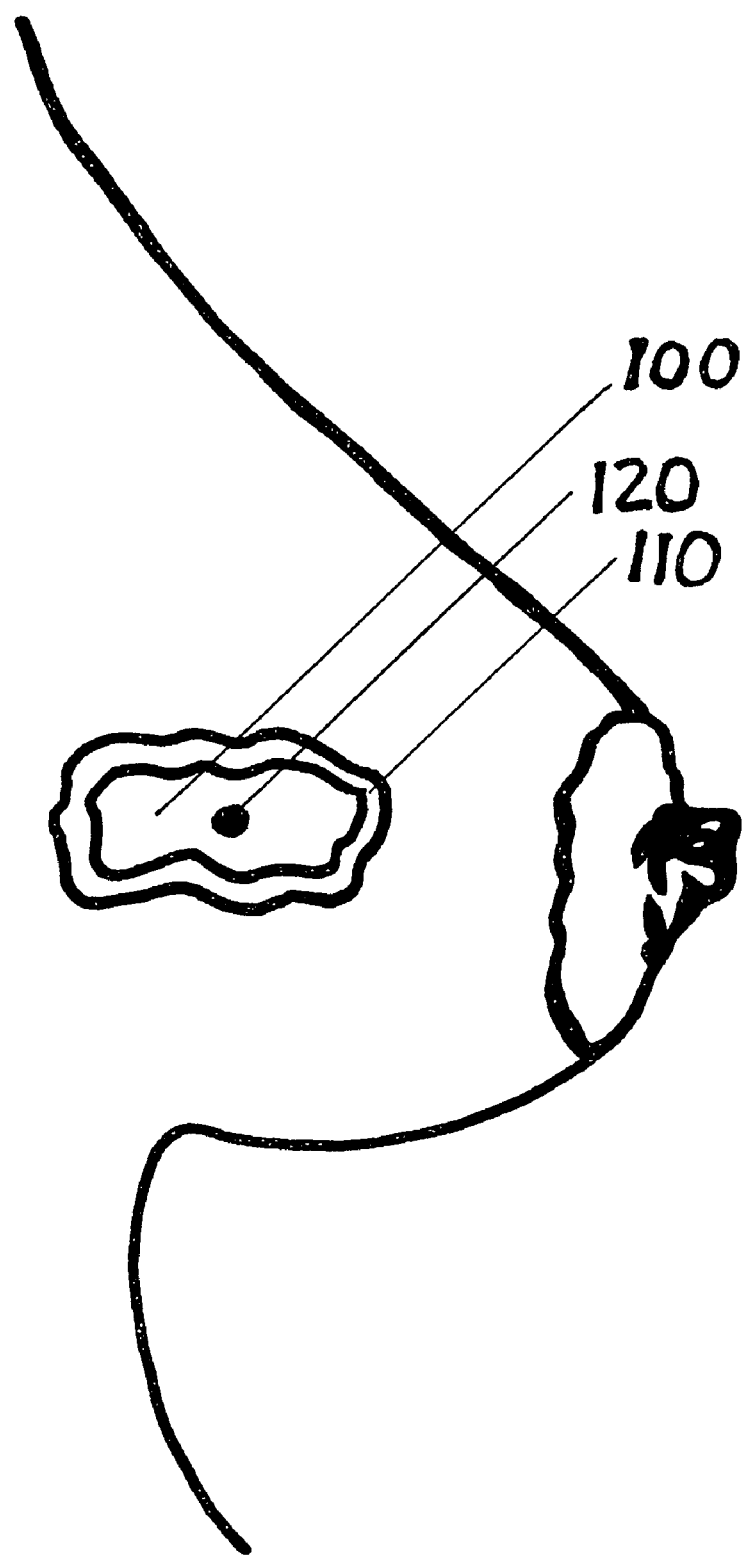
FIG. 7 depicts a partially re-absorbed implant containing a metallic marker within a shrinking breast lumpectomy cavity.

In FIG. 7, the resorbing implant (100) also contains one or more markers (120) to aid in targeting. Again, the implant and marker allow the treating physician to delay radiation treatment pending healing, chemotherapy or other favorable reasons for delay.

What is claimed is:

1. A method of partial breast radiation therapy comprising the steps of:
   placing within a breast cavity a substantially radio-opaque implant constructed of biocompatible and biodegradable material, said substantially radio-opaque implant supporting the tissue surrounding the breast cavity; and
   directing a radiation beam to said substantially radio-opaque implant serving as a target for delivery of radiation therapy to margins around the breast cavity, such that the radiation beam does not materially irradiate the whole of the breast.

2. The method of claim 1, wherein the radiation therapy is delivery of a therapeutically effective dosage of radiation to said breast tissue surrounding the implant via a stereotactic radiation machine.

3. The method of claim 2, wherein the radiation therapy is delivery of multiple therapeutically effective dosages of radiation to said breast tissue surrounding the implant in a single treatment via a stereotactic radiation machine.

4. The method of claim 2, wherein the radiation therapy is delivery of therapeutically effective dosages of radiation to said breast tissue surrounding the implant multiple times in a single treatment via a stereotactic radiation machine.

5. The method of claim 2 further comprising the step of initiating targeting of a radiation beam for delivery of radiation therapy occurs about 1-90 days subsequent placement of the implant.

6. The method of claim 1, wherein the radiation therapy is delivery of a therapeutically effective dosage of radiation to said breast tissue surrounding the implant via multidirectional radiation therapy.

7. The method of claim 6 further comprising the step of initiating targeting of a radiation beam for delivery of radiation therapy occurs about 1-90 days subsequent placement of the implant.

8. The method of claim 1, wherein the radiation therapy is delivery of a therapeutically effective dosage of radiation to said breast tissue surrounding the implant via image guided radiation therapy.

9. The method of claim 8 further comprising the step of initiating targeting of a radiation beam for delivery of radiation therapy occurs about 1-90 days subsequent placement of the implant.

10. The method of claim 1, wherein the radiation therapy is delivery of a therapeutically effective dosage of radiation to said breast tissue surrounding the implant via 3-D conformal radiation therapy.

11. The method of claim 10 further comprising the step of initiating targeting of a radiation beam for delivery of radiation therapy occurs about 1-90 days subsequent placement of the implant.

12. The method of claim 1, wherein the radiation therapy is delivery of a therapeutically effective dosage of radiation to said breast tissue surrounding the implant via intensity modulated radiation therapy.

13. The method of claim 1, wherein the breast cavity is a lumpectomy cavity, and further comprising the step of aspirating air from the lumpectomy cavity at any time after placement of the implant.

14. The method of claim 1 further comprising the step of initiating targeting of a radiation beam for delivery of radiation therapy occurs about 1-90 days subsequent placement of the implant.

15. The method of claim 1 further comprising the steps of initiating chemotherapy and thereafter, initiating targeting of a radiation beam for delivery of radiation therapy occurs up to 120 days subsequent placement of the implant.

16. The method of claim 1, wherein said substantially radio-opaque implant has a shape selected to guide the delivery of radiation therapy to the margins around said breast cavity.

17. The method of claim 1, wherein said substantially radio-opaque implant is constructed of a porous material.

18. A method of partial breast radiation comprising the steps of:
   placing within a breast lumpectomy cavity an implant constructed of biocompatible and biodegradable material with a substantially radio-opaque marker contained within the implant, and said implant supporting the tissue surrounding the breast lumpectomy cavity; and
   directing a radiation beam to said implant, said substantially radio-opaque marker within said implant serving as a target for delivery of radiation therapy to margins around the breast cavity, such that the radiation beam does not materially irradiate the whole of the breast.

19. The method of claim 18, wherein the radiation therapy is delivery of a therapeutically effective dosage of radiation to said breast tissue surrounding the implant or marker via a stereotactic radiation machine.

20. The method of claim 18, wherein the radiation therapy is delivery of multiple therapeutically effective dosages of radiation to said breast tissue surrounding the implant or marker in a single treatment via a stereotactic radiation machine.

21. The method of claim 18, wherein the radiation therapy is delivery of a therapeutically effective dosage of radiation to said breast tissue surrounding the implant or marker via multidirectional radiation therapy.

22. The method of claim 18, wherein the radiation therapy is delivery of a therapeutically effective dosage of radiation to said breast tissue surrounding the implant or marker via image guided radiation therapy.

23. The method of claim 18, wherein the radiation therapy is delivery of a therapeutically effective dosage of radiation to said breast tissue surrounding the implant or marker via 3-D conformal radiation therapy.

24. The method of claim 18, wherein the radiation therapy is delivery of a therapeutically effective dosage of radiation to said breast tissue surrounding the implant or marker via intensity modulated radiation therapy.

25. The method of claim 18 further comprising the step of aspirating air from the breast lumpectomy cavity at any time after placement of the implant.

26. The method of claim 18 further comprising the step of initiating targeting of a radiation beam for delivery of radiation therapy occurs about 1-90 days subsequent placement of the implant.

27. The method of claim 18 further comprising the step of initiating targeting of a radiation beam for delivery of radiation therapy occurs about 1-90 days subsequent placement of the implant.

28. The method of claim 18 further comprising the steps of initiating chemotherapy and thereafter, initiating targeting of a radiation beam for delivery of radiation therapy occurs up to 120 days subsequent placement of the implant.

29. The method of claim 18, wherein said implant has a shape selected to guide the delivery of radiation therapy to the margins around said breast lumpectomy cavity.

30. The method of claim 18, wherein the substantially radio-opaque marker is a radio-opaque element centrally located within said implant, said radio-opaque element being constructed from a material different from the material from which said implant is constructed.

* * * * *